United States Patent [19]
Masiello

[11] Patent Number: 5,834,443
[45] Date of Patent: Nov. 10, 1998

[54] COMPOSITION AND METHOD FOR TREATING HERPES SIMPLEX

[76] Inventor: Domenick J. Masiello, 47-44 Francis Lewis Blvd., Bayside, N.Y. 11361

[21] Appl. No.: 651,089

[22] Filed: May 21, 1996

[51] Int. Cl.$^6$ .......................... A61K 31/70; A61K 31/43
[52] U.S. Cl. ........................................ 514/44; 514/195.1
[58] Field of Search ................................... 514/44, 195.1

[56] References Cited

PUBLICATIONS

"Homeopathic Medical Repertory", R. Murphy, *Hahnemann Academy of North America*, First Edition, pp. 574–577, 1993.

"Homeopathic Therapeutics", Samuel Lilienthal, *B. Jain Publishers Pvt. Ltd.*, pp. 580–587, 1986.

"The Prescriber", J.H. Clarke, *Health Science Press*, pp. 224–225, 1972.

"Homeopathic Materia Medica", William Boericke, *Boericke & Runyon*, Nineth Edition, pp. 338, 341, 514–517, 1927.

"A Dictionary of Practical Materia Medica", J.H. Clarke, *Jain Publishing Co.*, pp. 802–813, 946–951, 1982.

"The Guiding Symptoms of our Materia Medica", C. Hering, *B. Jain Publishers Pvt. Ltd.*, pp. 116–131, 410–437, 1988.

"The Encyclopedia of Pure Materia Medica", R. Hughes et al, *B. Jain Publishers Pvt. Ltd.*, pp. 52–61, 502–519, 1988.

"Materia Medica of New Homeopathic Remedies", O.A. Julian, *Beaconsfield Publishers Ltd.*, pp. 432–435, 1990.

*Primary Examiner*—Zohreh Fay
*Attorney, Agent, or Firm*—Timothy J. Martin; Michael R. Henson

[57] ABSTRACT

The present invention broadly concerns the treatment of symptoms arising from outbreaks of herpes simplex viral infection. More particularly the invention is directed to the field of homeopathic medicine and the development of compositions and treatments for symptoms of the herpes simplex viral infections according to homeopathic medicine.

19 Claims, No Drawings

COMPOSITION AND METHOD FOR TREATING HERPES SIMPLEX

FIELD OF THE INVENTION

The present invention broadly concerns the treatment of symptoms arising from outbreaks of herpes simplex viral infections. More particularly, the invention is directed to the field of homeopathic medicine and the development of compositions and treatments for symptoms of the herpes simplex viral infections according to homeopathic techniques.

BACKGROUND OF THE INVENTION

Herpes simplex virus is generally known to be a recurrent viral infection which is characterized by the appearance on the skin or mucous membranes of either single or multiple clusters of small vesicles. These vesicles are filled with clear fluid and appear on slightly raised inflammatory bases. There are two primary types of herpes simplex virus (HSV) —HSV I and HSV II. Once contracted, the virus remains dormant in the nerve ganglia, but periodic eruptions are caused by overexposure to sunlight, stress, certain foods or drugs, or other unidentified causes. When an eruption occurs, lesions appear, usually on the mouth, lips, face, conjunctiva, cornea, buttocks or genitalia. However, these eruptions can occur anywhere on the skin or mucosa. These eruptions are both painful and often embarrassing to the person infected since HSV II is recognized as a venereal disease. Since there is no known cure for the disease itself, traditional medical therapy is directed to reducing the degree of pain or discomfort associated with the eruption. Among these, the compound known as acyclovir has been shown be fairly effective. Also, idoxuridiene and trifluridine are used on superficial infections. Treatment for HSV I, which normally manifest as outbreaks referred to as "cold sores" or "fever blisters" are traditionally treated with various moistening cremes, balms or ointments which are sold over-the-counter. Some desiccants, such as camphor, may also be used in treating HSV I.

While these compounds certainly have great value in lessening the pain attendant to the herpes event, there remains a long felt need for improved medications which may be effective in treating the symptoms arising from outbreaks of the herpes simplex viral infections. This, in part, is due to the provasive nature of herpes viral infections. Indeed, reported herpes infections in the United States was estimated to have increased from 25 Million people in 1980 to 44 Million people by 1990. Grange, *FAMILY PRACTICE NEWS*, (Jan. 1, 1996). Even though the classic presentation of herpes is multiple liaisons, the most common presentation is a single punctate lesion which heals within seven days. Often, patients who only experience only a single lesion chose not to see their doctor so that such cases go undiagnosed. This leads to the speculation that herpes is substantially more wide-spread than reported.

In addition to the medications for treating herpes which are produced by the allotropic pharmaceutical industry, the field of homeopathic medicine has also addressed herpes eruptions. Homeopathic medicine has its underpendings in what is referred to as the "law of similars". This approach follows a rule that, where a substance produces a specified disease symptom or indication at a high dosage level, that symptom will be effectively treated by a substantially dilute dose of the same substance. In other words, a symptom of a disease may be treated by a minor amount of a compound that will cause such symptom in a healthy person when administered at greater levels.

In order to demonstrate the effectiveness of a homeopathic drug, the drug is tested by a "proving" in order to see how the drug will effect an otherwise healthy person. Hundreds of compounds have been tested according to such "proving". Homeopathic repertories provide listings of the human anatomy and set forth symptoms that have been observed on such body part and treatments for the symptoms. On the other hand, books referred to as *"Materia Medicae"* set forth the homeopathic drugs and identify the maladies and symptoms each drug treats. More over, where a repertory lists a symptom, it classifies possible treating compounds as either first, second or third degree remedies for that symptom. Typically, a homeopathic practitioner will prescribe first degree indications for a particular symptom although sometimes second indications may be employed on a case-by-case basis. Very seldom would a homeopathic practitioner think to use a third degree indication and such listings are provided only to note that, on rare occasions, that the remedy has been known to cure the symptom but that it is not recognized by a "proving".

Finally, it should be noted that the homeopathic approach to treatment hypothesizes that the more a compound is diluted, the great curing or ameliorating effect it will have when used to treat a symptom. Thus, after a base preparation is made, either by an extract or maceration of an herbal compound or the dissolving of a selected compound in a solvent, a series of dilutions are prepared from the initial batch, called the "mother tincture". Homeopathic drugs are diluted according to either the decimal "X" or centesimal "C" scales. For a "3X" preparation, the mother tincture is diluted with nine parts of the desired diluent, in either liquid or powder form. The resultant mixture is then diluted a second time, in a ratio of one part mixture to ten parts solvent and the resulting mixture is diluted a third time in a ration of one to ten. Therefore, the 3X drug is actually at $10^{-3}$ potency of the mother tincture. Similarly, a 6X dilution would be at $10^{-6}$ potency of the original solution. In the "C scale" each dilution is done with ninety-nine parts diluent to the original mixture. Therefore, a 3C solution is at $10^{-6}$ potency of the original mixture and thus corresponds to a 6X potency. These scales are recognized by the Homeopathic Pharmacopeia of the United States (H.P.U.S.).

A variety of compounds are used in homeopathic medicine for the treatment of herpetic eruptions that have been observed historically in patients. The three compounds of interest in the present invention, however, are not generally recognized as effective treatments for a variety of herpes simplex eruptions. *Phytolacca decandra*, also known as poke-weed or garget weed has been identified as a first degree treatment for only a single type of herpetic skin eruption, namely, circinate eruptions of the skin. It has also been anecdotally observed as a third degree indication for circinatus herpetic eruptions of the head. A second compound *hypericum perforatum*, also known as St. John's Wort, has been noted to a second degree indication for herpetic skin eruptions. In each case, neither *phytolacca decandra* nor *hypericum perforatum* are thought to be primary or even significant treatments for herpes symptoms.

Despite the availability of allotropic pharmaceuticals for the treatment of outbreaks of herpes simplex viral infections, and further despite the availability of certain homeopathic treatments therefor, there remains a need for improved compositions which are effective in either treating or ameliorating the symptoms of such infections. There is a further need for improved homeopathic treatments of outbreaks of the herpes simplex viral infections. The present invention is directed to meeting those needs.

SUMMARY OF THE INVENTION

It is an object of the present invention to provide a new and useful composition that is effective in treating symptoms arising from outbreaks of herpes simplex viral infections.

It is a further object of the present invention to provide a new and useful homeopathic composition that can be used to treat and/or ameliorate the symptoms of herpes simplex viral infections.

Another object of the present invention is to provide a homeopathic composition which can be administered either orally or topically in the treatment of herpes simplex viral infections.

Still a further object of the present invention is to provide a homeopathic composition at selected potencies that effectively treats the symptoms arising from outbreaks of the herpes simplex virus.

According to the present invention, the homeopathic composition is disclosed for use in treating symptoms arising from outbreaks of herpes simplex viral infections. This homeopathic composition comprises a mixture that includes *phytolacca decandra, hypericum perforatum* and ribonucleic acid. Preferably, this mixture includes a first dilution of *phytolacca decandra* in a potency range of 3X to 12X H.P.U.S., a second dilution of *hypericum perforatum* in a potency range of 3X to 12X H.P.U.S. and a third dilution of ribonucleic acid in a potency range of 6X to 12X H.P.U.S. However, it is preferred that the first dilution be 6X H.P.U.S., the second dilution be 6X H.P.U.S. and a third dilution be 6X to 12X H.P.U.S. with the most preferred being 12X H.P.U.S. of the third dilution.

In any event, this mixture may include a pharmaceutically acceptable carrier solvent, preferably ethanol, and the mixture may be processed into a dosage unit selected from a group consisting of tablets, capsules, pellets (globules) and gel caps. Alternatively, the mixture includes a pharmaceutically acceptable topical preparation, preferably selected from a group consisting of ointments, cremes, lotions, liquids and gels. This topical preparation is preferably a hydrophilic ointment.

The present invention is also directed to a method of homeopathic treatment of symptoms arising from outbreaks of herpes simplex viral infections, with this method comprising the administering of an effective amount of a composition including *phytolacca decandra, hypericum perforatum* and ribonucleic acid. Preferably, the method according to the present invention uses the compositions as described above. In any event, the composition may be administered in a dosage unit wherein the dosage unit is prepared with about 0.001 milliliter of a solution containing a first dilution of *phytolacca decandra* in a first range of 3X to 12X H.P.U.S., a second dilution of *hypericum perforatum* in a second range of 3X to 12X H.P.U.S. and a third dilution of ribonucleic acid in a third range of 6X to 12X H.P.U.S.

The method also contemplates administering the composition in a dosage unit is in a dry form wherein the solution includes an ethanol carrier solvent and wherein the solution is placed in a selected quantity of a pharmaceutically acceptable dried compound and processed to allow a majority of the ethanol carrier solvent to evaporate. Moreover, the dosage unit may be administered orally three to four times per day until relief is achieved or the herpetic lesions disappear. The oral administration may include the step of placing the composition under the tongue of the patient. Alternatively, the method includes the application of the composition topically to the herpes simplex viral eruption three to four times per day.

These and other objects of the present invention will become more readily appreciated and understood from a consideration of the following detailed description of the exemplary embodiments.

DETAILED DESCRIPTION OF THE INVENTION

The present invention concerns a homeopathic composition for use in treating symptoms arising from outbreaks of herpes simplex viral infections. This invention also is directed to a method for the treatment of such symptoms using compositions according to the present invention. Broadly, the compositions, and thus the method, employs a mixture which includes three homeopathic compounds, namely, *phytolacca decandra, hypericum perforatum* and ribonucleic acid.

As noted in the background portion of this disclosure, homeopathic medicine is a system of curing diseases with very small doses of a remedy which, when administered in large doses to a healthy person, creates symptoms or conditions similar to that of the disease which is being treated by the homeopathic practitioner. The sum total of information developed about the symptoms which are treated by a particular remedy is referred to as its "*Materia Medica*". This information is typically accumulated over many years, especially through a technique called a homeopathic proving. A proving is essentially the single-blind administration of the remedy to healthy volunteers and the appearance of symptoms based upon such administration. Other sources of the "*Materia Medica*" for a particular compound are derived from clinical information of cured conditions and toxilogical data from accidental poisonings.

Many, but not all, homeopathic compounds are derived from plant or mineral sources. A "mother tincture", derived from the original source, is then diluted to a desired degree in order to form the resulting homeopathic drug. Thus, for purposes of the present invention, it is helpful to review the preparation of the mother tinctures and the subsequent dilutions of the three active ingredients, *phytolacca decandra, hypericum perforatum* and ribonucleic acid.

*Phytolacca decandra* is a naturally occurring branching herbaceous plant with a thick perennial root. It is indigenous to North America and grows abundantly in all parts of the United States. This plant is also known as Virginia Poke, Poke Root or garget weed. *Phytolacca decandra* is also found in northern portions of Africa, in southern portions of Europe as well as in numerous other countries.

*Phytolacca decandra* is generally prescribed in homeopathic medicine for aching, soreness, restlessness and prostration. It is preemmiently a glandular remedy known to have a powerful effect on fibrous and osseous tissues. Traditionally, this compound is used to treat syphilitic bone pains, chronic rheumatism, sore throat, quency and diphtheria as well as tenus and opisthotonos.

Hypericum perforatum is also naturally occurring plant also known as St. John's Wort. Its chief use in homeopathic medicine is in the treatment of wounds or injury to the nerves, especially fingers, toes and nails. It is also used as a treatment for pain and has been used to cure lock jaw.

Ribonucleic acid (RNA) has only recently become recognized by the homeopathic pharmacopeia of the United States (H.P.U.S.). RNA is a compound extracted from yeast. RNA generally appears as a powdered material.

The present invention employs a mixture of these three compounds in the form of dilutions of commercially available mother tinctures or, for RNA, the liquid attenuation.

*Phytolacca decandra* and *hypericum perforatum* mother tinctures are both Class C tinctures respectively having 55% and 65% alcohol content. The RNA employed is a 6X or other potency, class H liquid attenuation. Preferably, the first dilution of the *phytolacca decandra* is selected to be in a potency range of 3X to 12X H.P.U.S., but preferably 6X H.P.U.S. Similarly, the second dilution of *hypericum perforatum* is selected to be in a potency range of 3X to 12X H.P.U.S, but preferably 6X H.P.U.S. The desired third dilution of RNA, then, is selected to be in a range of 6X to 12X H.P.U.S., although it is preferred that the RNA third dilution be 12X H.P.U.S.

A homeopathic composition according to the present invention, is then prepared by mixing the first, second and third dilutions. The preferred composition is a mixture of *phytolacca decandra* 6X H.P.U.S., *hypericum perforatum* 6X H.P.U.S. and RNA 12X H.P.U.S., all in equal volumetric proportions. It should be noted, however, that successful results have been obtained where the dilution of RNA is 12X H.P.U.S. instead of 6X H.P.U.S.

In any event, after the dilutions are mixed together as a combined remedy, it may be processed into a dosage unit for the oral administration. Here, approximately two hundred and fifty #35 sugar pellets are moistened with approximately four drops (approximately 0.25 milliliter) of the combined remedy. According to the invention, then, a single dosage unit contains approximately 0.001 milliliter of the combined remedy. This dosage unit, then, could be administered either as a tablet, capsule, gel cap, pellet (globule) or other carrier, especially for oral administration. Indeed, the combined remedy could be administered in liquid form with a pharmaceutically acceptable carrier solvent, such as ethanol.

In addition to the oral formulation, the mixture of the three dilutions of *phytolacca decandra, hypericum perforatum* and ribonucleic acid could be formulated with a pharmaceutically acceptable topical preparation, such as an ointment, creme, lotion, liquid or gel. Preferably, the topical preparation would be in the form of a hydrophilic ointment. Here, approximately three to five percent by weight of the liquid remedy would be mixed with a hydrophilic ointment for direct application to the herpes eruptions.

When orally administered, it is preferred that one dosage unit be administered three to four times per day until relief is achieved or until the herpetic lesions disappear. Normally, a patient is instructed to orally take three dosage units at a time. The dosage unit may be placed under the tongue of the patient for such oral administration.

The effectiveness of the homeopathic composition according to the preferred embodiments of the present invention, that is, the *phytolacca decandra* (6X), *hypericum perforatum* (6X) and ribonucleic acid (6X or 12X) has been demonstrated as a remedy in treating the symptoms arising from outbreaks of the herpes simplex viral infection on a total of seventeen herpes eruptions experienced by five patients. These results are summarized as follows:

Patient #1

Patient #1 is a 40 year old white male who had been treated homeopathically since 1990 for a variety of medical problems including eczema, spastic colitis, and generalized arthralgias of the knees. He had also been treated osteopathically for chronic somatic dysfunction of the cervical and dorsal spine as well as somatic dysfunction of the shoulders related to postural strains secondary to his occupation. In May, 1995, the patient was diagnosed by a dermatologist as having genital herpes. The patient had several painful vesicles on the shaft of the penis which would recur periodically. He was initially treated homeopathically with Nitric Acid 200C on several occasions between May 1995 and August 1995. In January, 1996, the patient was given the composition (6X, 6X, 12X) to try on a "as needed basis". On his return visit of in February, 1996, the patient reported that the composition relieved the outbreak of herpes that he had a couple of weeks before. The relief took the form of a decrease in the intensity and duration of the pain and the eruptions.

Patient #2

Patient #2 is a 42 year old while female who originally presented in 1992 for the homeopathic treatment of multiple medical problems including obsessive compulsive disorder, frequent bouts of bronchitis, cardiac arrhythmia, seasonal allergies, chronic rhinitis, and chronic vaginal, anal and oral herpes for the past twenty years. The patient also had a past history of gonorrhea at age 17 but the herpes began in her early twenties. The oral, anal, and vaginal lesions have continued to recur periodically being brought on by stress, fatigue, and premenstrual tension.

In the Summer of 1994, the patient was given a sample of the initial composition (6X, 6X, 6X) ointment and was instructed to use it on an "as needed basis". Two months later, she had a mild outbreak of herpes which was dramatically relieved by the use of the ointment. There was a decrease in the amount of pain. One month later, she reported that she had an exceptionally bad outbreak of herpes which was completely resolved in about forty-eight hours. Her usual pattern is to have the symptoms last five to seven days. In February, 1995, she reported another outbreak of herpes which was helped by the use of this topical ointment.

Patient #3

Patient #3 is a 53 year old white female housewife who presented in May, 1994 for the treatment of menopausal syndrome, anal bleeding secondary to an anal fissure, and a persistent burning pain in her right forearm. She was diagnosed by her gynecologist as having vaginal herpes. The herpes were acquired in mid-1993. In July, 1994, the patient was given topical ointment (6X, 6X, 6X) ointment and told to use as needed for outbreaks of genital herpes. She was also instructed not to have unprotected intercourse with her husband. In September, 1994, the patient inquired whether she could use the ointment for a herpes lesion on one vaginal labrum which she described as looking like a "canker sore". she was instructed to use the ointment three times per day; she later reported that the herpetic eruption had resolved from the use of the ointment. The patient called again in October, 1995, to report a herpes outbreak and she was again advised to use the ointment three times per day. On a follow-up phone call, she noted that the herpes had resolved with the use of the ointment.

Patient #4

Patient #4 is a 47 year old white female who presented on July 24, 1993 for the treatment of several chronic medical conditions. About ten years previously, she had contacted several diseases such as gonorrhea, herpes of the genitals and the mucous lining of the nose and the lips, chronic intestinal parasites (giardia) and hepatitis A as well as hepatitis B. Normally weighing about 140 lbs., she had at her worst dwindled down to a mere 95 pounds. Ten years later, after many courses of antibiotics for the parasites she was still shedding them, had increased her weight to about 125 lbs., but still suffered from occasional bouts of nasal and genital herpes, chronic sinusitis, chronic bronchitis and chronic somatic dysfunction of the head and neck secondary to a motor vehicle accident more than twenty-five years again.

In April, 1994, she was given a sample of topical ointment (6X, 6X, 6X) and was told to use it "as needed". Over the two year test period, she reported numerous herpes outbreaks. With each application of the ointment, she reported that there was a decrease in the swelling of the eruptions and the surrounding tissue. There was also a decrease in the duration of the attack. The episodes before use of the ointment lasted about seven days, but with the use of the ointment they were lasting about four days.

Patient #5

Patient #5 is a 56 year white female school teacher who initially presented in July, 1988 for the treatment of chronic fatigue, chronic menstrual headaches, chronic lumbar backache and chronic herpes on the buttocks. Although most of her chronic symptoms had cleared during the next several years of homeopathic and osteopathic treatment, the chronic herpes remained a problem. The outbreaks had become less frequent; however, at times of emotional stress or profound fatigue from overwork, the lesions would return. In May, 1995, she was given a tube of the preferred ointment (6X, 6X, 12X); she was also given the oral form of the same formula (6X, 6X, 12X). the patient was instructed to use the oral drug as needed for the eruptions on her buttocks. In July, 1995, she reported that she had a very bad outbreak of herpes in early June, 1995. She used the ointment and took the oral dosage units and found the herpes lesions healed much faster than they had with previous homeopathic treatments.

From the foregoing data in the five test patients, it is concluded that the combination of the three homeopathic remedies have demonstrated surprising and unexpectedly good effects in the treatment of the symptoms of the herpes event. Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A homeopathic composition for use in treating symptoms arising from outbreaks of herpes simplex viral infections comprising a mixture including *phytolacca decandra, hypericum perforatum* and ribonucleic acid.

2. A homeopathic composition according to claim 1 wherein said mixture includes a first dilution of *phytolacca decandra* in a potency range of 3X to 12X H.P.U.S., a second dilution of *hypericum perforatum* in potency range of 3X to 12X H.P.U.S. and a third dilution of ribonucleic acid in a potency range of 6X to 12X H.P.U.S.

3. A homeopathic composition according to claim 1 wherein said first dilution is 6X H.P.U.S., said second dilution is 6X H.P.U.S. and said third dilution is in a potency range of 6X to 12X H.P.U.S.

4. A homeopathic composition according to claim 3 wherein said second dilution is 12X H.P.U.S.

5. A homeopathic composition according to claim 1 wherein said mixture is processed into a dosage unit selected from a group consisting of tablets, capsules, pellets (globules) and gel caps.

6. A homeopathic composition according to claim 1 wherein said mixture includes a pharmaceutically acceptable carrier solvent.

7. A homeopathic composition according to claim 6 wherein said carrier solvent is ethanol.

8. A homeopathic composition according to claim 1 wherein said mixture includes a pharmaceutically acceptable topical preparation.

9. A homeopathic composition according to claim 8 wherein said topical preparation is selected from a group consisting of: ointments, creams, lotions, liquids and gels.

10. A homeopathic composition according to claim 9 wherein said topical preparation is hydrophilic ointment.

11. A method for the homeopathic treatment of symptoms arising from an outbreak of herpes simplex viral infection comprising administering an effective amount of a composition including *phytolacca decandra, hypericum perforatum* and ribonucleic acid as a combined remedy.

12. A method according to claim 11 wherein said composition includes a first dilution of *phytolacca decandra* in a potency range of 3X to 12X H.P.U.S., a second dilution of *hypericum perforatum* in potency range of 3X to 12X H.P.U.S. and a third dilution of ribonucleic acid in a potency range of 6X to 12X H.P.U.S.

13. A method according to claim 12 wherein said third dilution is 12X H.P.U.S.

14. A method according to claim 11 wherein said composition is administered in a dosage unit wherein said dosage unit is prepared from approximately 0.001 milliliter of a solution containing a first dilution of *phytolacca decandra* in a first potency range of 3X to 12X H.P.U.S., a second dilution of *hypericum perforatum* in a second potency range of 3X to 12X H.P.U.S. and a third dilution of ribonucleic acid in a third potency range of 6X to 12X H.P.U.S.

15. A method according to claim 14 wherein said dosage unit is in a dry form wherein said solution includes an ethanol carrier solvent and wherein said solution is placed in a selected quantity of a pharmaceutically acceptable dry compound and processed to allow a majority of said ethanol carrier solvent to evaporate.

16. A method according to claim 14 wherein at least one dosage unit is administered orally three to four times per day until relief is achieved.

17. A method according to claim 16 wherein said dosage unit is placed under the tongue of a patient.

18. A method according to claim 11 wherein said composition is applied topically to a herpes simplex virus eruption.

19. A method according to claim 18 wherein said composition is applied three to four times per day.

* * * * *

UNITED STATES PATENT AND TRADEMARK OFFICE
CERTIFICATE OF CORRECTION

PATENT NO. : 5,834,443
DATED : November 10, 1998
INVENTOR(S) : Domenick J. Masiello It is certified that error appears in the above-identified patent and that said Letters Patent is hereby corrected as shown below:

Column 1,
Line 57, the word "allotropic" should be -- allopathic --.

Column 2,
Line 59, the word "allotropic" should be -- allopathic --.

Signed and Sealed this

Thirteenth Day of August, 2002

Attest:

Attesting Officer

JAMES E. ROGAN
Director of the United States Patent and Trademark Office